United States Patent [19]

Olson

[11] Patent Number: 4,672,028

[45] Date of Patent: Jun. 9, 1987

[54] COMPOSITIONS AND METHOD FOR SIMULTANEOUS MULTIPLE ARRAY OF ANALYTES USING RADIOISOTOPE CHELATE LABELS

[75] Inventor: Douglas R. Olson, Doylestown, Pa.

[73] Assignee: ICN Micromedic Systems, Inc., Costa Mesa, Calif.

[21] Appl. No.: 612,979

[22] Filed: May 23, 1984

[51] Int. Cl.$^4$ .................. G01N 33/53; G01N 33/567; G01N 33/536

[52] U.S. Cl. ............................................ 435/5; 435/7; 435/17; 435/26; 435/810; 436/500; 436/505; 436/510; 436/536; 436/542; 436/545; 436/804; 436/808; 436/811; 436/813; 436/814; 436/816; 436/817; 436/818; 436/820; 436/826

[58] Field of Search ............... 436/536, 542, 545, 500, 436/505, 510, 804, 808, 811, 813, 814, 817, 818, 816, 820, 826; 435/5, 7, 4, 17, 26, 810

[56] References Cited

U.S. PATENT DOCUMENTS

| | | | |
|---|---|---|---|
| 4,146,602 | 3/1979 | Gutcho et al. | 436/505 |
| 4,320,109 | 3/1982 | Wolf et al. | 436/540 |
| 4,338,248 | 7/1982 | Yokoyama et al. | 424/1.1 |
| 4,348,375 | 9/1982 | Goedemans | 424/1.1 |
| 4,385,046 | 5/1983 | Milbrath et al. | 424/1.1 |
| 4,432,907 | 2/1984 | Wieder et al. | 436/547 |

OTHER PUBLICATIONS

Sundberg et al, J. Medicinal Chem., 17(1974), 1304-7.
Hnatowich et al, J. Immunol. Meth., 65(1983), 147-57.
Hnatowich et al, Int. J. Appl. Radiat. Isot., 33 (1982), 327-32.
J. Radioanal. Chem., 53 (1979) pp. 327-336, Yeh et al.
Advances in Chemistry Series, No. 198, "Modification of Proteins", Meares et al., pp. 369-387.
"57Co: A Volume Mark for the TRIPLE-ISOTOPE, Double-Antibody Radioimmune Assay", in Immunochemistry, 1977, vol. 14.

Primary Examiner—Christine M. Nucker
Attorney, Agent, or Firm—Lyon & Lyon

[57] ABSTRACT

Compounds useful in a simultaneous multiple assay for analytes such as steroids, proteins, peptides, carbohydrates or drugs. The compound or compounds are prepared by labelling an individual analyte with a radioisotope through a chelating agent to form a coordinated compound. The assay uses one or more chelated labelled analytes with one or more labelled analytes wherein each radioisotope is different.

47 Claims, No Drawings

COMPOSITIONS AND METHOD FOR SIMULTANEOUS MULTIPLE ARRAY OF ANALYTES USING RADIOISOTOPE CHELATE LABELS

FIELD OF THE INVENTION

Radioimmunoassay is an analytical technique that resulted from the work of Berson and Yalow. In radioimmunoassay, radiolabelled exogenous antigen competes with unlabelled endogenous antigen for binding sites on an antibody or specific binding proteins, e.g. intrinsic factor, made specifically to the antigen.

The percentage of bound radiolabelled antigen decreases as a function of the increasing concentration of unlabelled antigen in the test sample. Separation of the bound and free radiolabelled antigen is necessary in order to determine the quantity of unlabelled antigen. This can be accomplished by insolubilization of the antigen-antibody complexes either by chemical means, e.g., polyethylene glycol precipitation, or by the addition of a second antibody directed toward the immunoglobulin present in the original antiserum, or by a combination of these two methods. The quantity of unlabelled antigen in an unknown sample is then determined by comparing the radioactivity of the precipitate, after centrifugation, with values established using known standards in the same assay system.

This invention relates to a method by which two or more analytes may be measured simultaneously in the same tube wherein the material to be assayed is radiolabelled. The invention also relates to the preparation of the labelled analytes employing chelating agents.

BACKGROUND OF THE INVENTION

There is a continuing search for cheaper and quicker analytical procedures. One way to accomplish this is to have an assay whereby two or more analytes can be assayed simultaneously in the same solution.

An example is in U.S. Pat. No. 4,146,602 issued on Mar. 27, 1979 which discloses a simultaneous assay of Folate and Vitamin $B_{12}$.

$Co^{57}$ is incorporated in Vitamin $B_{12}$ which is rather uncomplicated since Vitamin $B_{12}$ is a cobalt containing compound.

The problem was how to incorporate $Co^{57}$ into non-cobalt containing analytes.

The use of chelating agents is well known; however, there is no known use of chelating agents to prepare analytes useful in simultaneous assays.

A paper by Yeh et al. at pages 327–336 of *J. Radioanal Chem.*, 53, (1979) describes the preparation of an assay of indium chelates. A chapter in the American Chemical Society publication *Advances In Chemistry Series, No. 198 Modification of Proteins* by Meares et al. at pages 360–387 discusses chelate tagged proteins and polypeptides using cobalt to prepare radiopharmaceuticals.

Egan et al at pages 611–613 of a paper entitled "$^{57}Co$: A Volume Mark for the TRIPLE-ISOTOPE, Double-Antibody Radioimmune Assay" in *Immunochemistry*, 1977, Vol. 14, discusses using a chelating agent (EDTA) with cobalt; but to prevent adsorption of cobalt to serum proteins.

SUMMARY OF THE INVENTION

It has now been discovered that by employing chelating agents it is possible to label different analytes with different nuclides to now provide a method for more efficient and quicker assays on multiple analytes in a single tube, simultaneously.

Instruments are already being used to read radioactivity in a simultaneous assay (Vitamin $B_{12}$ and folate). Therefore, this invention will not require any new techniques or instrumentations.

One aspect of the invention is the preparation of the radioactive labelled analytes using a chelating agent by which the labelled metal is attached to the analyte through a chelating agent.

Another aspect is the radioactive labelled analyte itself which is a coordinated compound.

Still another aspect is the use of said analyte(s) in a radioimmunassay procedure.

By the use of this invention one can place a metal isotope on any suitable analyte to assay for said analyte.

Another aspect is the metal isotope labeling of purified antibodies to said analyte(s) to construct an immunoradiometric assay (IRMA).

The essence of the invention is the introduction of radionuclides into analytes by way of analyte-bound chelating moieties and the subsequent use of the radiolabelled analytes in radioassays.

The chelators may be of a variety of materials satisfying the following criteria:

(1) they must be capable of forming covalent linkages with the analytes of interest;

(2) once attached to the analytes, they must retain their ability to form coordination complexes with $+2$ and $+3$ metal radionuclides; and (3) the formed complexes of analyte, chelator, and metal radionuclides must retain all or part of the binding specificity or antigenicity of the native analyte.

Radiolabelled analytes containing individually distinguishable radionuclides may be combined in a variety of configurations such that one or more analytes may be measured simultaneously by radioassay. Analytes labelled in this described manner could also be combined with analytes labelled by alternate means to provide simultaneous radioassays.

The choice of radionuclides to be utilized for labelling is governed by the following practical considerations.

(1) they must have a sufficiently long half-life to enable them to be used over a practical period of time (eg. several months);

(2) they must be available in sufficiently high specific activity to provide an adequate signal amplification; and (3) they must possess a relatively unique emmission spectrum when used in combination with one or more other radionuclides.

The method of assaying comprises employing a coordinated compound of the general formula:

metal isotope—chelator—organic species    I

Examples of analytes which can be employed include any organic species which can react with a chelating agent. In general, they are steroids such as estrogens, progesterone, digoxin, cortisol, 17-hydroxyprogesterone and the like; proteins, such as human chorionic gonadotropin, luteinizing hormone, follicle stimulating hormone, thyroid stimulating hormone, alpha-fetoprotein, trypsin, hepatitis associated antigen, carcinoembryonic antigen and the like; peptides, such as ACTH, endorphins, angiotensin, insulin and the like;

carbohydrates, such as pneumococal polysaccharides and the like; drugs, such as cocaine, tetrahydrocannibinol, barbaturates, amphetamines and the like; antibiotics, such as gentamicin, and the like; also, the labeled antibodies to these analytes can be used.

Specific pairs of analytes which could be analyzed simultaneously include the following:

1. Carcinoembryonic Antigen (CEA) —hCG, fetoprotein, or any other two tumor markers;
2. LH/FSH;
3. Hepatitis B Surface Antigen/Hepatitis B Core Antigen or any other two viral antigens;
4. Thyroxine/Thyroid Stimulating Hormone in Screening for neonatal hypothyroidism;
5. Thyroxine/Thyroid Binding Globulin (for T3U) in diagnosis and treatment of adult thyroid disease;
6. Angiotensin II/Renin in diagnosing cause for hypertension;
7. Adrenocorticotrophic Hormone (ACTH)/Cortisol in differentiating primary from secondary adrenal disease;
8. Insulin/C-Peptide in the diagnosis and treatment of diabetes;
9. Estriol/Human Placental Lactogen in monitoring pregnancy;
10. Lactate Dehydrogenase (LDH)/Creatine Phosphokinase (CKP) Isoenzymes in diagnosing heart disease; and
11. Serological Screening for Donor Blood for any two viruses or venereal infections simultaneously, such as hepatitis-B Surface Antigen and human T-Cell leukemia virus antigens or antibodies to same. Chelating agents which can be used include aminopolycarboxylates of the following general formula:

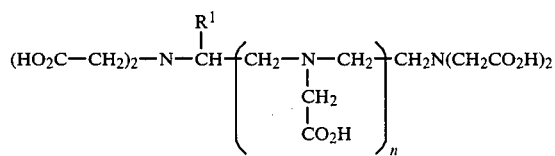

wherein R' is phenyl or substituted phenyl wherein the substituents are $NO_2$, $NH_2$ and $SO_3H$ and the like and n is an integer of 0 or 1 such as ethylenediamine tetraacetic acid (EDTA), ethylene dinitrilotetraacetic acid, diethylenetriaminepentaacetic acid and derivatives thereof such as 1-(p-bromoacetimidobezyl)-EDTA.

In general any radioisotope of a metal can be employed; however, practical considerations dictate that only those with half lifes of a reasonable period of time be employed. However, it should be understood that even isotopes of a relatively short half life can be employed in this invention.

Preferred isotopes include those of the metals, cobalt, iron, indium, technetrum, europium and terbium.

Especially preferred are isotopes of iron and colbalt with colbalt 57 and iron 59 being most preferred.

The labelled analytes are prepared by reacting the chelating agent with the analyte at a temperature in the range of from about 4° to about 40° C. in a basic solution of a solvent such as sodium bicarbonate (0.1M).

After purification by passing the reaction mixture through molecular sieves, such as Sephadex G75, or comparable polyacrylamides or other polymeric molecular sieves, the purified product is treated with the metal isotope at a temperature in the range of from 4° C. to 40° C. in the presence of a buffer from sodium acetate (metal free), potassium acetate and the like.

A key to the formation of these compounds is the discovery that the buffers must be metal-free to obtain the best products.

The following examples illustrate the preparation of labelled analytes.

EXAMPLE 1

Preparation of 57 Cobalt Labeled LH

One mg of lyophilized LH is dry mixed with 3.8 mg of diethylenetriamine pentaacetic anhydride (DTPA). 100 μl of metal-free 0.1M sodium bicarbonate is added and the reaction vortexed. (metal free buffers are prepared by passing buffer solutions through metal chelating ion exchange resins such as BioRad Chelex ® 100). After thirty minutes at room temperature, the reaction miture is passed through a Sephadex G75 column equilibrated and eluted with 0.5M acetate buffer pH 5.8 (metal free). The LH-DTPA containing fractions are identified by absorbance at 280 nm. Peak fractions are pooled and diluted to 100 μg LH/ml with 0.5M acetate buffer pH 5.8.

100 μl of LH-DTPA (10 μg) are added to 10 μl (500 μCi) of carrier-free 57 cobalt chloride in 0.5N HCl and reacted for one and one-half hours at room temperature. The reaction mixture is passed through a Sephadex G75 column equilibrated and eluted with phosphate buffered saline (PBS) containing 0.1% bovine albumin. The $^{57}$Co-DTPA-LH elutes near the void volume as a single peak. In general >70% of the $^{57}$Co is chelated by the LH-DTPA precursor yielding tracers with specific activities ranging from 36 to 43 μCi/μg.

EXAMPLE 2

Preparation of $^{125}$I Labeled FSH

This procedure describes the process for the preparation of FSH-$I^{125}$ tracer for an iodination size of 5 mCi, which will yield 2 to 2.5 mCi of usable tracer.

37.5 μl of FSH antigen at a concentration of 1 mg/ml in 0.01M PBS is added to a solution of 50 μl of 0.4M phosphate buffer, pH 7.4 and sodium I-125 (5 mCi) and vortexed. The reaction is initiated by the addition of 10 μl of chloromine-T (1 mg/ml 0.1M phosphate buffer, pH 7.2) to the reaction mixture and vortexed. The reaction is terminated after 25 seconds at room temperature by the addition of 25 μl of sodium metabisulfite (1 mg/ml in 0.1M phosphate buffer, pH 7.4) to the reaction mixture and vortexing.

Immediately after termination, the reaction mixture is transferred to a Sephadex G-75 column (0.5×18.0 cm) equilibrated in 0.01M PBS, 0.1% BSA. The column is eluted with 0.02M PBS/BSA and 0.5 ml fractions are collected. The FSH I-125 elutes between fraction numbers 10-20. All fractions which are on the ascending and decending sides of the peak which contain greater than 40% of the activity of the peak tube are pooled. The pooled fractions are diluted with 0.01M PBS/BSA to a concentration of approximately 100 Ci/ml. The diluted tracer is treated with a 5 ml slurry of Bio-Rad AG-21K resin (rinsed and resuspended in 0.01M PBS, 3% BSA) and stored overnight at 4° C.

By substituting for the tracer analyte and chelating agent in examples 1 and 2 and by following substantially the procedures described therein, the following radiolabelled tracers can be prepared.

| Ex. | Tracer | Analyte | Chelating Agent |
|---|---|---|---|
| 3 | $^{57}Co$ | LH | DTPA |
| 4 | $^{51}Cr$ | FSH | DTPA |
| 5 | $^{111}In$ | TSH | phenyl EDTA |
| 6 | $^{57}Co$ | T4 | DPTA |
| 7 | $^{57}Co$ | FSH | DPTA |
| 8 | $^{57}Co$ | TSH | phenyl EDTA |
| 9 | $^{57}Co$ | Ferritin | DTPA |
| 10 | $^{57}Co$ | Rabbit anti TSH | DTPA |
| 11 | $^{57}Co$ | TSH | DTPA |

The following is an example of the types of hormones which can be employed in the assay procedure to be followed and the reagents which are required for the assay.

Analytes

Luteinizing hormone (LH) and follicle stimulating hormone (FSH) are glycoproteins synthesized and secreted by the basophil (beta) cells of the anterior pituitary in response to gonadotropin releasing hormone (GnRH) produced by the hypothalamus. Both hormones consist of two polypeptide chains designated "alpha" and "beta". The amino acid sequence of the "alpha" subunits is similar for the two hormones as well as TSH and HCG. The "beta" subunits however, are unique and confer immunological specificity, biological specificity and biological activity for the two molecules.

In the female, LH and FSH regulate ovarian changes during the menstrual cycle. FSH promotes maturation of the Graafian follicle and ovum while LH is necessary for the development of a functioning corpus luteum and the production of progesterone. Circulating levels of LH and FSH are controlled by separate negative-feedback mechanisms on the hypothalamus.

In the male, FSH stimulates production of spermatozoa in the seminiferous tubules. Both FSH and LH promote testosterone secretion by the interstitial cells or Leydig tissue of the testes. Testosterone and other steroid hormones control circulating levels of LH and FSH by negative-feedback effects on the hypothalamus.

The measurement of LH and FSH is an important tool for evaluating disorders of the hypothalamic/pituitary/gonadal axis. Hypopituitarism due to pituitary dysfunction in both males and females may result in a hypogonadal state characterised by low levels of LH and FSH (hypogonadotropic hypogonadism). On the other hand, elevated levels of LH and FSH (hypergonadotropic hypogonadism) may indicate a hypogonadal state caused by primary gonadal failure although LH levels may be normal if androgen secretion is preserved.

In the female, the mid-cycle LH peak is a good indication that ovulation will occur within the next 24 hours. Thus, subfertile couples can be informed of impending ovulation. Such knowledge is also important in timing laparoscopy for oocyte retrieval and subsequent in vitro fertilization.

Reagents

LH Cobalt 57 Tracer Solution

LH tracer is prepared as described above and diluted to a concentration of approximately $0.02\mu$ Ci/ml in 0.01M PBS, 0.1% BSA, 5% normal rabbit serum and 0.1% sodium azide.

FSH $^{125}I$ Tracer Solution

The FSH tracer solution is diluted in 0.01M PBS, 0.1% BSA, 5% normal rabbit serum, and ion exchange resin strip, and 0.1% sodium azide to a concentration of approximately $0.02\mu$ Ci/ml.

LH/FSH Antiserum Solution

Each antisera is diluted in 0.01M PBS, 10 mM EDTA, 0.1% BSA, and 0.1% sodium azide at a titer sufficient to bind approximately 30% of the radiolabelled antigens.

LH/FSH Precipitating Solution

Goat anti-rabbit IgG immune serum is diluted in 0.01M PBS, 5% polyethylene glycol and 0.1% sodium azide at a titer sufficient to precipitate 100 microliters of 5% normal rabbit serum.

LH/FSH Standards

Seven concentrations of LH/FSH standards, 0/0, 5/2.5, 10/5, 25/10, 60/25, 120/50, 240/100 mIU/mL are prepared in 0.01M PBS, 0.1% BSA, and 0.1% sodium azide.

LH/FSH Controls

Control samples are prepared in 0.01M PBS, 0.1% BSA and 0.1% sodium azide.

Preparation of Reagents

Combine equal volumes of LH $^{57}Co$ tracer solution and FSH $^{125}I$ tracer solution. 50 $\mu l$ of each tracer are required for each assay tube.

Specimen Collection and Preparation

Human serum or plasma samples should be used. If the assay is to be run on the day of specimen collection, store the sample at 4° C. until assayed. If the assay is to be run at a later date, store sample frozen at $=20°$ C. Allow the sample to thaw prior to assay; mix thoroughly. Heterogeneity of specimens after thawing has been shown to result in misleading assay values. The sample should be rejected for assay if it is radioactively contaminated from a previous in vivo diagnostic procedure. A fresh sample should be drawn after sufficient time has passed for the elimination of the radioactivity from the body.

Radioimmunoassay Procedure

Before proceeding with the assay, bring all reagents, sample and assay tubes to room temperature. A standard curve must be performed with each series of unknowns. See FIG. I for flow chart of this procedure.

1. Label 12×75 mm assay tubes according to the following outline:

| ASSAY TUBE | CONTENTS | |
|---|---|---|
| T, T | Total Counts | |
| 1,2 | Blank Tubes | |
| 3,4 | Standard: | 0 mIU/Ml |
| 5,6 | | 5 mIU/mL LH |
| | | 2.5 mIU/mL FSH |
| 7,8 | | 10 mIL/mL LH |
| | | 5 mIU/mL FSH |
| 9,10 | | 25 mIU/mL LH |
| | | 10 mIU/mL FSH |
| 11,12 | | 60 mIU/mL LH |
| | | 25 mIU/mL FSH |
| 13,14 | | 120 mIU/mL LH |
| | | 50 mIU/mL FSH |
| 15,16 | | 240 mIU/mL LH |
| | | 100 mIU/mL LH |
| 17,18 | CI Control Sample | |
| 19,20 | CII Control Sample | |
| 21,100 | Patient Sample | |

2. Accurately pipette 200$\mu$ uL of the ZERO STANDARD into the blank tubes and 200$\mu$ of STANDARDS of patient samples into appropriately labeled assay tubes.

3. Pipette 100 μl of ANTISERUM SOLUTION into all tubes except Total Count and Blank tubes and vortex.

4. Incubate at 37° C. for 1 hour.

5. Pipette 100 μl of TRACER SOLUTION into all tubes and vortex.

6. Incubate at room temperature (22±3° C.) for 1 hour.

7. Shake the PRECIPITATING SOLUTION immediately before use. Pipette 1.0 mL into all tubes except total count tubes. Vortex tubes thoroughly.

8. Incubate at room temperature (22±3° C.) for 10 minutes.

9. Centrifuge for 15 minutes at 1000×g.

10. Decant the liquid from each assay tube and blot rims of tubes on absorbent material.

11. Count tubes on gamma counter set respectively for $I^{125}$ and $Co^{57}$ for FSH and LH.

Figure 1
ASSAY PROCEDURE - FLOW CHART

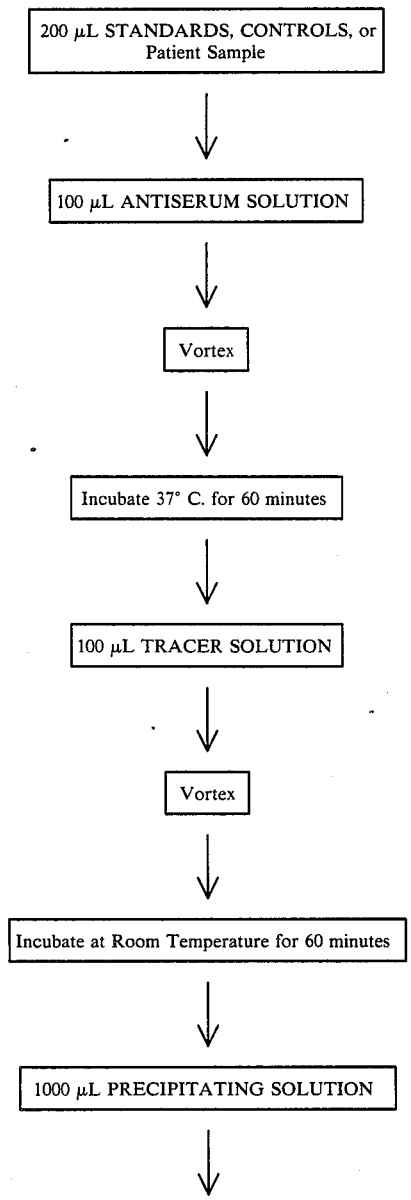

-continued
Figure 1
ASSAY PROCEDURE - FLOW CHART

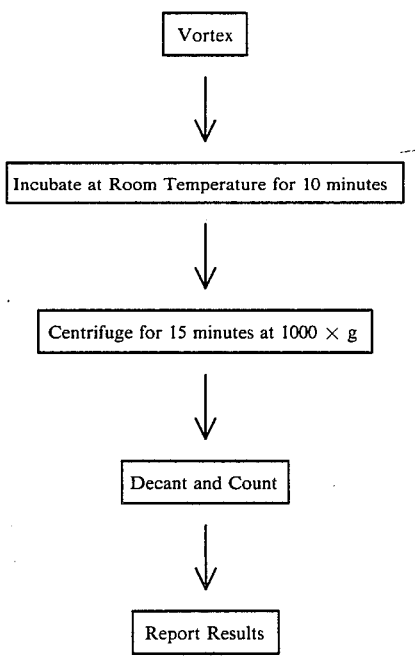

Procedural Notes

1. Establish a repetitive time pattern for addition of antibody, tracer, and precipitating antibody from the beginning to the end of the assay and for decantation.

2. Be sure all droplets are removed from the rims after decanting.

3. Consistent results occur between assays when a constant room temperature is maintained.

NOTE: The gamma counter must discriminate adequately between $^{125}$I and $^{57}$Co. Counters that do not permit low crossover between channels or that do not offer adequate stability are unsatisfactory for this assay. Since the energy peaks of Co-57 and I-125 overlap, the windows of the gamma counter must be adjusted to assure <3% crossover. Do not omit this consideration as there is no proportionality in values obtained on an unadjusted instrument and the accuracy of the test would be decreased.

Using $I$-125 source: $\dfrac{\text{CPM from } Co\text{-57 channel}}{\text{CPM from } I\text{-125 channel}} \times$ 100 = % crossover of $I$-125 into $Co$-57 channel Using $Co$-57 source: $\dfrac{\text{CPM from } I\text{-125 channel}}{\text{CPM from } Co\text{-57 channel}} \times$ 100 = % crossover of $Co$-75 into $I$-125 channel Calculation of Results 1. Average the counts per minute (CPM) for all duplicate tubes. Correct for nonspecific binding by subtracting the average CPM's of tubes 3 and 4 from all other counts.

2. Calculate the % Binding (B/Bo) by dividing the averaged CPM's for the standard and samples by the averaged CPM's of the ZERO STANDARD (tubes 5 and 6) and multiply by 100.

$$\text{Percent Binding } (B/Bo) = \frac{CPM \text{ of Standard or Sample}}{CPM \text{ of ZERO STANDARD}} \times 100$$

3. Prepare a standard curve on 3-cycle log-logit graph paper by:
   (a) Plotting the percent binding (B/Bo) or averaged CPM for each standard concentration on the Y (logit or linear, ordinate) axis and the standard concentration values (mIU/ml LH or FSH) on the X (logarithmic, abscissa) axis.
   (b) Draw a straight line through the data points. No attempt should be made to extrapolate the curve beyond the range employed.

4. Read the unknown patient samples from the standard curve (concentration is read off the X axis where patient CPM or % binding intersects the curve).

Typical raw data is shown in Table I and typical standard curves are shown in FIG. 2. These curves are FOR REFERENCE ONLY and should NOT be used for calculation by any value.

TABLE I

Typical Data

| Tube No. | Contents | CPM Bound | LH Average Corrected CPM | % B/Bo | Patient Value mIU/ml | CPM Bound | FSH Average Corrected CPM | % B/Bo | Patient Value mIU/ml |
|---|---|---|---|---|---|---|---|---|---|
| 1, 2 | Totals | 90,410 90,576 | 86,927 | | | 67,802 67,808 | 67,805 | | |
| 3, 4 | Assay Blank | 3,750 3,548 | | | | 1,962 1,816 | | | |
| 5, 6 | 0 | 13,602 13,884 | 10,094 | 100 | | 16,494 16,422 | 14,579 | 100 | |
| 7, 8 | 5/2.5 | 12,476 12,212 | 8,691 | 86.1 | | 14,348 14,160 | 12,363 | 84.8 | |
| 9, 10 | 10/5 | 11,574 10,578 | 7,429 | 73.6 | | 13,010 11,920 | 10,570 | 72.5 | |
| 11, 12 | 20/10 | 9,428 9,626 | 5,875 | 58.2 | | 9,638 9,654 | 7,756 | 53.2 | |
| 13, 14 | 50/25 | 7,584 7,154 | 3,725 | 36.9 | | 5,648 5,635 | 3,747 | 25.7 | |
| 15, 16 | 100/50 | 6,018 5,992 | 2,352 | 23.3 | | 3,833 3,725 | 1,895 | 13.0 | |
| 17, 18 | 200/100 | 4,984 5,034 | 1,363 | 13.5 | | 2,801 3,057 | 1,035 | 7.2 | |
| 19, 20 | Control I | 8,952 9,194 | 5,424 | 53.7 | 25.5 | 5,248 5,500 | 3,485 | 23.9 | 30.0 |
| 21, 22 | Control | 7,678 7,680 | 4,030 | 39.9 | 45.0 | 9,930 10,484 | 8,318 | 57.1 | 8.7 |

EXPECTED VALUES (20-31)

| Normals | | LH mIU/ml | FSH mIU/ml |
|---|---|---|---|
| Female: | Follicular phase | 0–14 | 2–10 |
| | Mid-cycle peak | 10–70 | 9–18 |
| | Luteal phase | 0–16 | 0–9 |
| | Post menopause | 20–70 | 20–100 |
| Male: | | 0–9 | 2–10 |

Published LH and FSH ranges amy differ because of variations in calibration, method, and/or technique. Each laboratory must confirm its own normal range of a representative sample population.

Performance Characteristics

Precision is the extent to which a given set of measurements of the same sample agrees with the mean.

Results of Intra- And Inter-assay Variation:

| | LH Intra-Assay | LH Inter-Assay | FSH Intra-Assay | FSH Inter-Assay |
|---|---|---|---|---|
| Pool 1 | | | | |
| X (mIU/ml) | 19.4 | 19.4 | 6.2 | 6.2 |
| s (mIU/ml) | 1.4 | 1.9 | 0.5 | 0.2 |
| CV (%) | 7.1 | 9.6 | 7.7 | 3.3 |
| n | 15 | 15 | 15 | 15 |
| m | 3 | 3 | 3 | 3 |
| Pool 2 | | | | |
| X (mIU/ml) | 41.6 | 41.6 | 18.0 | 18.0 |
| s (mIU/ml) | 2.1 | 2.5 | 0.9 | 1.0 |
| CV (%) | 5.0 | 6.1 | 5.2 | 5.5 |
| n | 15 | 15 | 15 | 15 |
| m | 3 | 3 | 3 | 3 |
| Pool 3 | | | | |
| X (mIU/ml) | 97.6 | 97.6 | 46.3 | 46.3 |
| s (mIU/ml) | 8.4 | 12.5 | 2.1 | 2.7 |
| CV (%) | 8.6 | 12.8 | 4.6 | 5.8 |
| n | 30 | 30 | 30 | 30 |
| m | 6 | 6 | 6 | 6 |

Sensitivity

Sensitivity is the smallest amount of unlabelled antigen that can be distinguished from no antigen. The sensitivity of the assay is 1.7 mIU/ml for LH and 1.1 mIU/ml for FSH based on 95% B/Bo.

Accuracy

Accuracy is the extent to which a given measurement of a substance agrees with the known value of that substance.

(A) Spike Recovery

Two normal male base pools were spiked with five levels of LH and FSH. Results are shown on the following table:

| | LH | | FSH | |
|---|---|---|---|---|
| LH/FSH added (mIU/ml) | X Added Recovered (mIU/ml) | % LH Recovered | X Added Recovered (mIU/ml) | % FSH Recovered |
| 10/5 | 12.2 | 122 | 6.3 | 127 |
| 20/10 | 21.0 | 105 | 11.7 | 117 |
| 40/20 | 41.7 | 104 | 21.6 | 108 |
| 80/40 | 83.4 | 104 | 46.1 | 115 |
| 160/80 | 130.5 | 82 | 65.8 | 82 |

(B) Correlation with Other Methods

A patient sample correlation was run against three individual LH radioimmunoassays and three individual FSH radioimmunoassays. A least squares linear regression analysis was then carried out on paired values obtained in the LH and FSH RIA KIT procedure against each of the references. The results are summarized below:

LH:
  Method A = 0.949 + 1.8 n = 28, $r^2$ = 0.918
  Method B = 1.314 − 1.6 n = 28, $r^2$ = 0.959
  Method C* = 0.438 + 5.1 n = 33, $r^2$ = 0.911

*Standards for this method are calibrated against 2nd IRP-HMG. All other methods are calibrated against 1st IRP 68/40.

FSH:
  Method C = 1.045 − 2.8 n = 23, $r^2$ = 0.893
  Method D = 1.686 − 2.1 n = 30, $r^2$ = 0.977
  Method E** = 0.473 − 1.1 n = 30, $r^2$ = 0.983

** Standards for this method are calibrated against 2nd IRP-HMG. All other methods are calibrated against 1st IRP 69/194.

Specificity

Specificity is the extent of freedom from interference by substances other than the one intended to be measured. The degree of specificity of the antibody for the antigen represents one of the most significant advantages of any radioimmunoassay procedure.

The cross-reactivity of structurally similar hormones at fifty percent binding are given in the following table:

| | RELATIVE ACTIVITY* | |
|---|---|---|
| COMPOUND | LH ASSAY | FSH ASSAY |
| LH | 1.000 | <0.0035 |
| FSH | 0.085 | 1.000 |
| HCG | 0.261 | <0.0028 |
| TSH | <0.001 | <0.0010 |

*Relative activity is calculated on a unit/unit basis except for TSH which is calculated on a weight/weight basis.

What is claimed:

1. A composition useful in a simultaneous assay which comprises two or more radioisotope-labeled compounds in a substantially metal-free solution, one or more of said compounds being stable coordinated compounds of the formula radioisotope—chelator—analyte, wherein each radioisotope in said composition is different.

2. The composition according to claim 1 useful in a simultaneous assay wherein the analyte portion of one or more of said stable coordinated compounds is formed from a steroid, a protein, a peptide, a carbohydrate or a drug, and wherein each radioisotope in said composition is different.

3. The composition according to claim 2 useful in a simultaneous assay wherein the analyte portion of one or more of said stable coordinated compounds is formed from estrogen, progesterone, digoxin, cortisol, 17-hydroxyprogesterone, human chorionic gonadotropin, luteinizing hormone, follicle stimulating hormone, thyroid stimulating hormone, alphafetoprotein, trypsin, $T_3$, $T_4$, hepatitis associated antigen, carcinoembryonic antigen, ACTH, endorphins, angiotensin, insulin, pneumococcal polysaccharides, cocaine, tetrahydrocannibinol, barbiturate, an amphetamine, gentiamycin, Vitamin $B_{12}$ or folate, and wherein each radioisotope in said composition is different.

4. The composition according to claim 3 useful in a simultaneous assay wherein the analyte portion of one or more of said stable coordinated compounds is formed from luteinizing hormone, $T_3$, $R_4$, follicle stimulating hormone, thyroid stimulating hormone, Vitamin $B_{12}$ or folate, and wherein each radioisotope in said composition is different.

5. The composition according to claim 4 useful in a simultaneous assay wherein the analyte portion of one or more of said stable coordinated compounds is formed from thyroid stimulating hormone or follicle stimulating hormone, and wherein each radioisotope in said composition is different.

6. The composition according to claim 5 useful in a simultaneous assay wherein the analyte portion of one or more of said stable coordinated compounds is formed from a chelator of the formula:

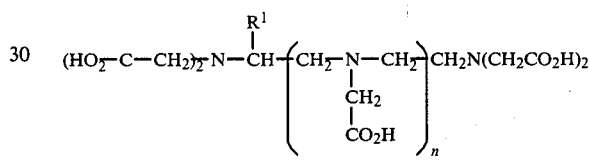

wherein $R^1$ is phenyl or substituted phenyl wherein the substituent is selected from $NO_2$, $NH_2$ or $SO_3H$ and n is an integer of 0 or 1, and wherein each radioisotope in said composition is different.

7. The composition according to claim 6 useful in a simultaneous assay wherein the analyte portion of one or more of said stable coordinated compounds is formed from a chelating agent selected from ethylenediaminetetraacetic acid, ethylene dinitrilotetraacetic acid, diethylenetriaminepentaacetic acid or derivatives thereof, and wherein each radioisotope in said composition is different.

8. The composition according to claim 7 useful in a simultaneous assay wherein the analyte portion of one or more of said stable coordinated compounds is formed from ethylenediaminetetraacetic acid, and wherein each radioisotope in said composition is different.

9. The composition according to claim 8 useful in a simultaneous assay wherein the radioisotope portion of one or more of said stable coordinated compounds is formed from cobalt, iron, iodine, technetium, europium or terbium, and wherein each radioisotope in said composition is different.

10. The composition according to claim 9 useful in a simultaneous assay wherein the radioisotope portion of one or more of said stable coordinated compounds is formed from cobalt or iron, and wherein each radioisotope in said composition is diifferent.

11. The composition of claim 1 wherein there are two stable coordinated compounds wherein the analyte portions are formed from carcinoembryonic antigen and β-HCG.

12. The composition of claim 11 wherein there are two stable coordinated compounds wherein the analyte portions are formed from leutinizing hormone and thyroid stimulating hormone.

13. The composition of claim 11 wherein there are two stable coordinated compounds wherein the analyte portions are formed from hepatitis B-surface antigen and hepatitis B-core antigen.

14. The composition of claim 11 wherein there are two stable coordinated compounds wherein the analyte portions are formed from thyroxine and thyroid stimulating hormone.

15. The composition of claim 11 wherein there are two stable coordinated compounds wherein the analyte portions are formed from thyroxine and thyroid binding globulin.

16. The composition of claim 11 wherein there are two stable coordinated compounds wherein the analyte portions are formed from angiotensin-II and renin.

17. The composition of claim 11 wherein there are two stable coordinated compounds wherein the analyte portions are formed from adrenocorticotrophic hormone and cortisol.

18. The composition of claim 11 wherein there are two stable coordinated compounds wherein the analyte portions are formed from insulin and C-peptide.

19. The composition of claim 11 wherein there are two stable coordinated compounds wherein the analyte portions are formed from estriol and human placental lactogen.

20. The composition of claim 1 wherein there are two stable coordinated compounds wherein the analyte portions are formed from lactate dehydrogenase and creatine phosphokinase.

21. The composition of claim 1 wherein there are two stable coordinated compounds wherein the analyte portions are formed from hepatitis B-surface antigen and human T-cell leukemia virus.

22. In a simultaneous multiple assay for two or more analytes, which assay includes the steps of:
    (a) contacting a sample and a mixture of radioisotope-labeled compounds in the presence of a mixture of binders for said analytes.
    (b) separating bound portions of the analytes from unbound portions of the analytes, and
    (c) counting radioactivity of at least one of the bound and unbound portions to determine the radioisotope-labeled compounds in the bound or unbound portions;
    the improvement comprising the condition that said mixture of radioisotope-labeled compounds is of the composition of claim 1.

23. In a simultaneous multiple assay for two or more analytes, which assay includes the steps of:
    (a) contacting a sample and a mixture of radioisotope-labeled compounds in the presence of a mixture of binders for said analytes,
    (b) separating bound portions of the analytes from unbound portions of the analytes, and
    (c) counting radioactivity of at least one of the bound and unbound portions to determine the radioisotope-labeled compounds in the bound or unbound portions;
    the improvement comprising the condition that said mixture of radioisotope-labeled compounds is of the composition of claim 2.

24. In a simultaneous multiple assay for two or more analytes, which assay includes the steps of:
    (a) contacting a sample and a mixture of radioisotope-labeled compounds in the presence of a mixture of binders for said analytes,
    (b) separating bound portions of the analytes from unbound portions of the analytes, and
    (c) counting radioactivity of at least one of the bound and unbound portions to determine the radioisotope-labeled compounds in the bound or unbound portions;
    the improvement comprising the condition that said mixture of radioisotope-labeled compounds is of the composition of claim 3.

25. In a simultaneous multiple assay for two or more analytes, which assay includes the steps of:
    (a) contacting a sample and a mixture of radioisotope-labeled compounds in the presence of a mixture of binders for said analytes,
    (b) separating bound portions of the analytes from unbound portions of the analytes, and
    (c) counting radioactivity of at least one of the bound and unbound portions to determine the radioisotope-labeled compounds in the bound or unbound portions;
    the improvement comprising the condition that said mixture of radiosotope-labeled compounds is of the composition of claim 4.

26. In a simultaneous multiple assay for two or more analytes, which assay includes the steps of:
    (a) contacting a sample and a mixture of radioisotope-labeled compounds in the presence of a mixture of binders for said analytes,
    (b) separating bound portions of the analytes from unbound portions of the analytes, and
    (c) counting radioactivity of at least one of the bound and unbound portions to determine the radioisotope-labeled compounds in the bound or unbound portions;
    the improvement comprising the condition that said mixture of radioisotope-labeled compounds is of the composition of claim 5.

27. In a simultaneous multiple assay for two or more analytes, which assay includes the steps of:
    (a) contacting a sample and a mixture of radioisotope-labeled compounds in the presence of a mixture of binders for said analytes,
    (b) separating bound portions of the analytes from unbound portions of the analytes, and
    (c) counting radioactivity of at least one of the bound and unbound portions to determine the radioisotope-labeled compounds in the bound or unbound portions;
    the improvement comprising the condition that said mixture of radioisotope-labeled compounds is of the composition of claim 6.

28. In a simultaneous multiple assay for two or more analytes, which assay includes the steps of:
    (a) contacting a sample and a mixture of radioisotope-labeled compounds in the presence of a mixture of binders for said analytes,
    (b) separating bound portions of the analytes from unbound portions of the analytes, and
    (c) counting radioactivity of at least one of the bound and unbound portions to determine the radioisotope-labeled compounds in the bound or unbound portions;
    the improvement comprising the condition that said mixture of radioisotope-labeled compounds is of the composition of claim 7.

29. In a simultaneous multiple assay for two or more analytes, which assay includes the steps of:
(a) contacting a sample and a mixture of radioisotope-labeled compounds in the presence of a mixture of binders for said analytes,
(b) separating bound portions of the analytes from unbound portions of the analytes, and
(c) counting radioactivity of at least one of the bound and unbound portions to determine the radiosotope-labeled compounds in the bound or unbound portions;
the improvement comprising the condition that said mixture of radioisotope-labeled compounds is of the composition of claim 8.

30. In a simultaneous multiple assay for two or more analytes, which assay includes the steps of:
(a) contacting a sample and a mixture of radioisotope-labeled compounds in the presence of a mixture of binders for said analytes,
(b) separating bound portions of the analytes from unbound portions of the analytes, and
(c) counting radioactivity of at least one of the bound and unbound portions to determine the radioisotope-labeled compounds in the bound or unbound portions;
the improvement comprising the condition that said mixture of radioisotope-labeled compounds is of the composition of claim 9.

31. In a simultaneous multiple assay for two or more analytes, which assay includes the steps of:
(a) contacting a sample and a mixture of radioisotope-labeled compounds in the presence of a mixture of binders for said analytes,
(b) separating bound portions of the analytes from unbound portions of the analytes, and
(c) counting radioactivity of at least one of the bound and unbound portions to determine the radioisotope-labeled compounds in the bound or unbound portions;
the improvement comprising the condition that said mixture of radioisotope-labeled compounds is of the composition of claim 10.

32. A kit useful in simultaneous multiple assay of one or more analytes comprising:
a mixture of binders for said analytes;
a mixture of radioisotope-labeled compounds, said mixture being of the composition of claim 1;
means for contacting a sample with said mixture of rdioisotope-labeled compounds in the presence of said mixture of binders; and
means for separating bound portions of the analytes from unbound portions of the analytes.

33. A kit useful in simultaneous multiple assay of one or more analytes comprising:
a mixtures of binders for said analytes;
a mixture of radiosotope-labeled compounds, said mixture being of the composition of claim 2;
means for contacting a sample with said mixture of radioisotope-labeled compounds in the presence of said mixture of binders; and
means for separating bound portions of the analytes from unbound portions of the analytes.

34. A kit useful in simultaneous multiple assay of one or more analytes comprising:
a mixture of binders for said analytes;
a mixture of radioisotope-labeled compounds, said mixture being of the composition of claim 3;
means for contacting a sample with said mixture of radioisotope-labeled compounds in the presence of said mixture of binders; and
means for separating bound portions of the analytes from unbound portions of the analytes.

35. A kit useful in simultaneous multiple assay of one or more analytes comprising:
a mixture of binders for said analytes;
a mixture of radioisotope-labeled compounds, said mixture being of the composition of claim 4;
means for contacting a sample with said mixture of radioisotope-labeled compounds in the presence of said mixture of binders; and
means for separating bound portions of the analytes from unbound portions of the analytes.

36. A kit useful in simultaneous multiple assay of one or more analytes comprising:
a mixture of binders for said analytes;
a mixture of radioisotope-labeled compounds, said mixture being of the composition of claim 5;
means for contacting a sample with said mixture of radioisotope-labeled compounds in the presence of said mixture of binders; and
means for separating bound portions of the analytes from unbound portions of the analytes.

37. A kit useful in simultaneous multiple assay of one or more analytes comprising:
a mixture of binders for said analytes;
a mixture of radioisotope-labeled compounds, said mixture being of the composition of claim 6;
means for contacting a sample with said mixture of radioisotope-labeled compounds in the presence of said mixture of binders; and
means for separating bound portions of the analytes from unbound portions of the analytes.

38. A kit useful in simultaneous multiple assay of one or more analytes comprising:
a mixture of binders for said analytes;
a mixture of radioisotope-labeled compounds, said mixture being of the composition of claim 7;
means for contacting a sample with said mixture of radioisotope-labeled compounds in the presence of said mixture of binders; and
means for separating bound portions of the analytes from unbound portions of the analytes.

39. A kit useful in simultaneous multiple assay of one or more analytes comprising:
a mixture of binders for said analytes;
a mixture of radioisotope-labeled compounds, said mixture being of the composition of claim 8;
means for contacting a sample with said mixture of radioisotope-labeled compounds in the presence of said mixture of binders; and
means for separating bound portions of the analytes from unbound portions of the analytes.

40. A kit useful in simultaneous multiple assay of one or more analytes comprising:
a mixture of binders for said analytes;
a mixture of radioisotopes-labeled compounds, said mixture being of the composition of claim 9;
means for contacting a sample with said mixture of radioisotope-labeled compounds in the presence of said mixture of binders; and
means for separating bound portions of the analytes from unbound portions of the analytes.

41. A kit useful in simultaneous multiple assay of one or more analytes comprising:
a mixture of binders for said analytes;

a mixture of radioisotope-labeled compounds, said mixture being of the composition of claim 10;

means for contacting a sample with said mixture of radioisotope-labeled compounds in the presence of said mixture of binders; and means for separating bound portions of the analytes from unbound portions of the analytes.

42. A composition useful in simultaneous assay which comprises the composition of claim 1 and an analyte labeled with I-125.

43. A composition useful in simultaneous assay which comprises the composition of claim 2 and an analyte labeled with I-125.

44. A composition useful in simultaneous assay which comprises the composition of claim 3 and an analyte labeled with I-125.

45. A composition useful in simultaneous assay which comprises the composition of claim 4 and an analyte labeled with I-125.

46. A composition useful in simultaneous assay which comprises the composition of claim 5 and an analyte labeled with I-125.

47. A composition according to claim 46 wherein the coordinated compound analyte is leutinizing hormone and the analyte labeled with I-125 is follicle stimulating hormone.

* * * * *